United States Patent
Wewers et al.

(10) Patent No.: US 6,647,783 B2
(45) Date of Patent: Nov. 18, 2003

(54) VENT PLUG FOR ENVIRONMENTALLY CONTROLLED HOUSING FOR GAS MONITORING SYSTEM

(75) Inventors: Frank J. Wewers, Lenexa, KS (US); Brian K. EuDaly, Louisburg, KS (US)

(73) Assignee: Manning Systems, Inc., Lenexa, KS (US)

( * ) Notice: Subject to any disclaimer, the term of this patent is extended or adjusted under 35 U.S.C. 154(b) by 0 days.

(21) Appl. No.: 09/948,384

(22) Filed: Sep. 8, 2001

(65) Prior Publication Data

US 2003/0046975 A1 Mar. 13, 2003

(51) Int. Cl.$^7$ ............................. G01P 11/10; G01N 27/00
(52) U.S. Cl. ............................................. 73/431; 422/98
(58) Field of Search ................ 73/23.2, 23.21, 73/431; 236/DIG. 19; 361/690; 454/1.84; 422/98, 83

(56) References Cited

U.S. PATENT DOCUMENTS

| | | |
|---|---|---|
| 3,864,628 A | 2/1975 | Klass et al. |
| 3,999,122 A | 12/1976 | Winstel et al. |
| 4,040,990 A | 8/1977 | Neely |

(List continued on next page.)

OTHER PUBLICATIONS

Sales Brochure of Manning Systems, Inc., for Single Gas Elecrochemical Sensor/Transmitter, Model EC, believed to have been published more than one year prior the filling of the present application.
Sales Brochure of Manning Systems, Inc., for Ammonia Selective Electrochemical Gas Sensor/Transmitter, Model EC–NH$_3$believed to have been published more than one year prior the filing of the present application.

A sheet of drawings including three figures showing a vent plug of the type shown in the Sales Brochure of Manning Systems, Inc., for Ammonia Selective Electrochemical Gas Sensor/Transmitter, Model EC–NH$_3$, believed to have been published more than one year prior the filing of the present application. The vent plug shown therein was on sale more than one year prior to the filing of the present application.

The vent plugs include a gas permeable membrane extending across an inner end of the plug. The prior art vent plug is adapted to be mounted in a vent plug opening in a housing for a gas sensor. The vent plug has an outer portion adapted to be mounted against the housing. Vent holes are formed in the outer portion, which also includes a cylindrical rim or wall extending through the vent plug opening into the housing. A gas permeable, paper membrane extends across an inner end of the cylindrical wall. Gripping fingers are formed in the cylindrical wall of the plug and are adapted to engage the housing around the vent hole to hold the plug in place. Slots or open space extend around the gripping fingers to permit the gripping fingers to flex relative to the cylindrical wall.

*Primary Examiner*—Hezron Williams
*Assistant Examiner*—J Z P
(74) *Attorney, Agent, or Firm*—Shughart Thomson & Kilroy P.C.

(57) ABSTRACT

A monitoring system, such as used to monitor the presence and/or concentration of gases or other such fluids, includes a housing through which fluid is permitted to pass and which includes a heater element. The housing includes one or more vent hole/vent plug combinations and fluid, including gas and/or liquid, passes through the vent hole/vent plug combinations to flow into, through and/or out of the housing. A heater element is located in the housing and maintains the housing interior above the dew point to facilitate proper operation of the sensor element. The heater element, in conjunction with the vent hole/vent plug combinations, facilitates a heated-air plume through the housing to avoid the build up of moisture therein and to expose the sensor element to a steady stream of ambient atmosphere for monitoring the gas concentrations in same.

15 Claims, 4 Drawing Sheets

U.S. PATENT DOCUMENTS

| | | |
|---|---|---|
| 4,171,341 A | 10/1979 | Morgan |
| 4,256,985 A | 3/1981 | Goodson et al. |
| 4,350,660 A | 9/1982 | Robinson et al. |
| 4,407,778 A | 10/1983 | Shiratori et al. |
| 4,481,499 A | 11/1984 | Arima et al. |
| 4,644,333 A | 2/1987 | Barendsz et al. |
| 4,745,796 A | 5/1988 | Abdelrahman et al. |
| 4,839,331 A | 6/1989 | Maroldo et al. |
| 4,911,892 A | 3/1990 | Grace et al. |
| 5,057,436 A | 10/1991 | Ball |
| D397,629 S * | 9/1998 | Wewers ................ D10/96 |
| 5,879,631 A | 3/1999 | Wewers et al. |

\* cited by examiner

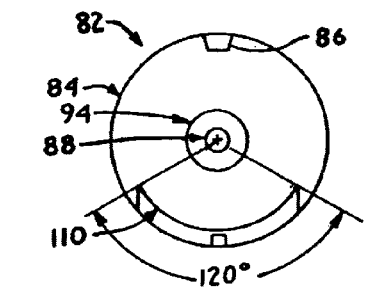
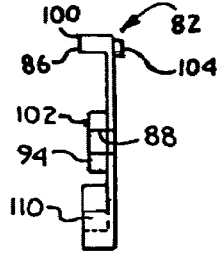
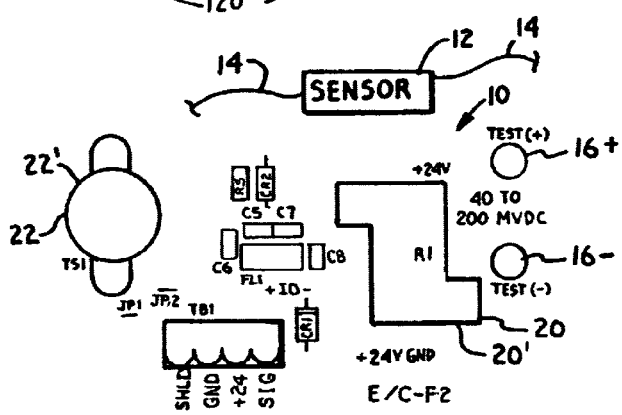
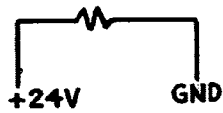
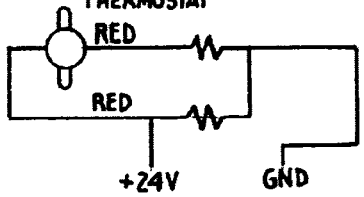
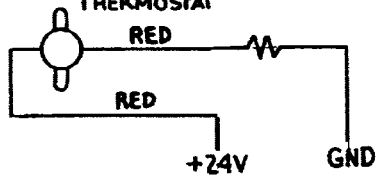

VENT PLUG FOR ENVIRONMENTALLY CONTROLLED HOUSING FOR GAS MONITORING SYSTEM

BACKGROUND OF THE INVENTION

In many industries and situations, it is necessary to sample the atmosphere in a defined area. The sampling is used to monitor environmental conditions and can be conducted periodically or continuously.

One common application of such monitoring is to sample the atmosphere for levels of certain gases. Leak detection is a prime example. Leak detection is often used in refrigeration systems, air conditioning systems, systems where carbon monoxide or other harmful gases may be present, and the like. The chemical industry and the food storage industry are examples of industries that use such monitoring systems. Gases that are often monitored include $NH_3$, $CO_2$, $H_2$, $Cl_2$, CFCs, HCFCs, HFCs, $CH_4$, $O_2$ and the like. Upon sensing a predetermined condition, such monitoring systems generate signals indicating gas concentrations above prescribed limits. The typical system responses include triggering alarms, summoning help and controlling (e.g., shutting down) equipment, etc.

Various sensor technologies measure selected PPM (parts per million) setpoints from OSHA's Permissible Exposure Limit (PEL) and the Threshold Value Limit/Short-Term Exposure Limit (TVL-STEL) up to the Lower Explosive Limit (LEL) range and indicate concentration levels with bargraph displays. Field-adjustable setpoints allow an operator to set or adjust warning and alarm trip levels at a main control panel.

One specific gas monitoring system manufactured and sold by Manning Systems, Inc. of Lenexa, Kans., identified by the name GM-10, includes three types of visual status indications for each of a plurality of channels. A warning LED indicates that the operator-selected warning setpoint has been exceeded, and the system includes elements to trigger a common warning relay and an individual warning relay for that channel on an optional relay board. The alarm LED operates in a similar manner for the alarm level, but also triggers a common horn relay and a buzzer relay which can be cleared manually. A fault on any channel triggers a common fault and horn relays and the buzzer. When any channel goes into a specified trip condition by sensing element levels beyond a setpoint, common relays for Warning, Alarm, Fault and/or auxiliary Horn are activated. An optional plug-in communication port for Ethernet or MOD-BUS connection provides remote monitoring of the system status/alarm functions. The GM-10 monitor uses diffusion for gas detection and provides continuous monitoring of a wide range of areas. Several areas can be monitored simultaneously. The GM-10 monitor can interface to, but can operate independently of, plant control systems.

Manning Systems, Inc. also manufactures and sells a sensor under the name EC which comprises a pair of polarized electrodes isolated from ambient air by a gas permeable membrane. As gas diffuses into a sensor, a redox reaction occurs generating a current linearly proportional to gas concentration. Readouts of the model EC have built-in visual and audible alarms, as well as relay output for ventilation fan activation, central alarm tie-in and the like. In addition, the EC model can provide direct input into PLCs and computer control systems.

As used herein, the term "fluid" includes gas as well as liquid.

Many sensors used in monitoring systems are sensitive to temperature, humidity, contamination or other such environmental conditions. If the environmental conditions are not within a certain specified range, the readings of the sensors associated with the monitoring system can be slow or suspect. Extreme environmental conditions can also deteriorate sensor performance and ultimately contribute to the sensor failure.

Therefore, there is a need for a monitoring system which can maintain the environment around a sensor within a specified range.

For example, if a monitoring system is used in a refrigeration system, conditions adjacent to the sensor may create a humidity condition that is out of the specified range for accurate and reliable operation of the monitoring system. Furthermore, a cycle of freezing and warming may degrade certain elements of the monitoring system, especially when combined with a high humidity environment. Condenser coils in refrigerated facilities also tend to contribute to high moisture levels. For example, when the coils are defrosted significant amounts of moisture are obtained therefrom, which often refreezes and coats the walls, ceilings, etc. of large, commercial freezers. Such ice coatings can significantly compromise the performance of prior art sensors, particularly those with externally-mounted sensor elements which are susceptible to ice coating because they are exposed. Gas sensing problems are also encountered when the temperature around the sensor element is at or near the dew point, whereby reliable readings are difficult to obtain.

Therefore, there is a need for a monitoring system that can ensure that the humidity and temperature in the vicinity of humidity and/or temperature sensitive instruments of the monitoring system are maintained within specified ranges.

Still further, some monitoring systems may be located in areas that are periodically washed, as by applying high pressure washing fluid to the area. The washing fluid from the washing process may lodge on or near the sensor or other equipment of the monitoring system and can create an undesirable condition which may adversely affect the readings of the system.

Therefore, it is desirable to efficiently remove any fluid used to clean a monitored area from the environment adjacent to a sensor and its associated equipment of a monitoring system.

Therefore, there is a need for a monitoring system from which fluid may be efficiently removed.

Previous monitoring systems included fluid-tight sealed housings or enclosures. These were intended to protect certain sensor components, such as the electronics, microprocessors, etc. from the adverse effects of exposure to harsh ambient conditions within the extreme environments being monitored. Monitoring was accomplished by mounting the sensor element externally. The enclosure structures for housing the electronics and other protected components were typically impervious materials such as metal or plastic, with fluid-tight seals and/or gaskets providing the necessary sealing for covers and access panels. Standards promulgated by the National Electrical Manufacturers Association (NEMA) provided ratings for different levels of airtight security, with NEMA Class 4 being the highest. NEMA Class 4 enclosures were often specified for extreme environments. However, this configuration of enclosures has several disadvantages. For example, even the tightest enclosure is susceptible to trace amounts of air infiltration, whereby moisture and other degrading elements can accumulate in the housing interiors. Moreover, the seals and gaskets are subject to deterioration over time, thus further compromising the operation of the sensors and contributing to false readings, etc. Still further, the externally-mounted sensor elements are susceptible to moisture-related degradation with corresponding performance degradation.

Therefore, there is a need for a monitoring system in which proper environmental conditions adjacent to the sensor and other equipment can be maintained without being subject to or vitiated by improper sealing or closure of a housing of the monitoring system. Preferably NEMA Class 1 enclosures can be utilized for cost effectiveness.

Furthermore, temperature and humidity conditions may cause condensation to form in the monitoring system, even in an air-tight housing. Such condensation may create problems for the sensor or its associated elements or the readings of the monitoring system. Accumulated condensation can turn to ice or frost in certain conditions. Ice or frost may adversely affect the operation and/or reliability of the monitoring system, including the sensor and its related circuitry. At best, the elements of the monitoring system will have to be designed to account for the presence of ice and/or frost, which may either inhibit versatility of the system or make it more expensive to purchase, install and maintain.

Therefore, there is a need for a monitoring system that can control the humidity near humidity-sensitive elements and that can control the formation of ice and/or frost therein.

Previous sensor systems include 110 volt AC circuits for which conduits were run to the sensor enclosures. However, connecting such conduits to the sensor enclosures presented potential problems associated with moisture infiltration. For example, the conduits themselves can be infiltrated with moisture, which in some installations (particularly with top-entry conduits) can trickle down into the enclosures, causing damage to the electronics therein. Moreover, 110 volt AC systems tended to be susceptible to power interruptions, which in many cases rendered the systems inoperable.

Accordingly, there is a need for a monitoring system which operates on low voltage, direct current electrical power, which does not require large electrical conduits (particularly top-mounted conduits), and which can be maintained in continuous operation with battery backup in the event of a power outage.

SUMMARY OF THE INVENTION

The above-discussed disadvantages and drawbacks are overcome by a monitoring system that maintains desired environmental conditions adjacent to a sensor and any elements associated therewith by maintaining temperature in those locations within a desired range and permitting the atmosphere surrounding the monitor to circulate past the sensor and/or its related equipment as well as into, through and out of a housing for the sensor and its related components.

In this manner, desired environmental conditions can be efficiently and precisely maintained in areas where such conditions are important to proper functioning of the monitoring system.

Specifically, the monitoring system of the present invention includes a housing for a sensor and the circuitry related to the monitoring functions of the system. The housing includes a heater which may have a thermostat control associated therewith. The heater is located in a position to effectively maintain selected components, such as the sensor and its related electronic components, at a temperature within a desired range, and the thermostat is located to accurately control the heater to fulfill that function. The monitoring system of the present invention further permits fluid, including atmospheric air as well as liquids, to flow into, through and out of the housing. Atmospheric circulation through the housing is accounted for and thus the housing need not be sealed.

The combination of a temperature-controlled housing interior, minimal liquid ingression and controlled flowing atmosphere through the housing permits the monitoring system of the present invention to be used in a variety of situations without being degraded or having the performance thereof degraded due to undesired environmental effects.

For example, humidity, temperature and the like are properly controlled in the monitoring system of the present invention and ranges kept within acceptable limits, even in a cycling situation whereby monitoring system performance is consistent and reliable. Any fluid applied to the monitoring system during an area cleaning process will readily exit the monitoring system and the system is formed of materials that can readily dry under the influence of fluid, such as air, flowing through the housing of the monitoring system. System performance is not dependent on seals, gaskets, membranes or the like. Still further, the circulation through the monitoring system housing will remove contaminants from the housing when desired.

TECHNICAL FIELD OF THE INVENTION

The present invention relates to the general art of housings and containers, and to the particular field of housings for electrical devices.

OBJECTS AND ADVANTAGES OF THE INVENTION

It is a main object of the present invention to provide a monitoring system that can maintain conditions around selected components within specified ranges.

It is another object of the present invention to provide a monitoring system in which temperature conditions near temperature-sensitive components can be maintained within desired ranges.

It is another object of the present invention to provide a monitoring system from which fluid can readily be drained.

It is another object of the present invention to provide a monitoring system in which desired conditions adjacent to selected components can be maintained without being subject to or vitiated by improper sealing or closure of a housing used in the monitoring system.

It is another object of the present invention to provide a monitoring system in which humidity conditions near humidity-sensitive components can be maintained within desired ranges.

It is another object of the present invention to provide a monitoring system in which the dew point near dew point-sensitive components can be maintained within desired ranges.

It is another object of the present invention to provide a housing that can be used in connection with Model GM-10 and/or Model EC from Manning Systems, Inc. monitoring equipment in a monitoring system.

It is another object of the present invention to provide a housing which encloses the sensor element and associated circuitry for protection against direct contact with water, dust and other detrimental elements while simultaneously providing a plume of ambient atmosphere upwardly through the enclosure.

It is another object of the present invention to provide a housing that maintains a positive temperature differential between internal and external air whereby air encountering the sensor element can be maintained above the dew point to avoid saturation of the sensor element and the associated sensor circuitry.

It is another object of the present invention to provide a gas sensor and an environmentally-controlled housing therefor which can be mounted in various installations, including refrigerated facilities, rooftops, exterior areas, etc.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 9 shows an inner portion of the vent plug included in the monitoring system of the present invention.

FIG. 10 is a side elevational view of the vent plug inner portion shown in FIG. 9.

FIG. 11 is a block diagram of a sensor embodying the present invention, particularly showing the general layout of a circuit board thereof.

FIG. 12 is a schematic diagram of a heater resistor circuit with a warm, low or high heat resistor.

FIG. 13 is a schematic diagram of a heater resistor circuit with two low heat resistors and a thermostat.

FIG. 14 is a schematic diagram of a heater resistor circuit with a high heat resistor and a thermostat.

DETAILED DESCRIPTION OF THE INVENTION

Figure 1:
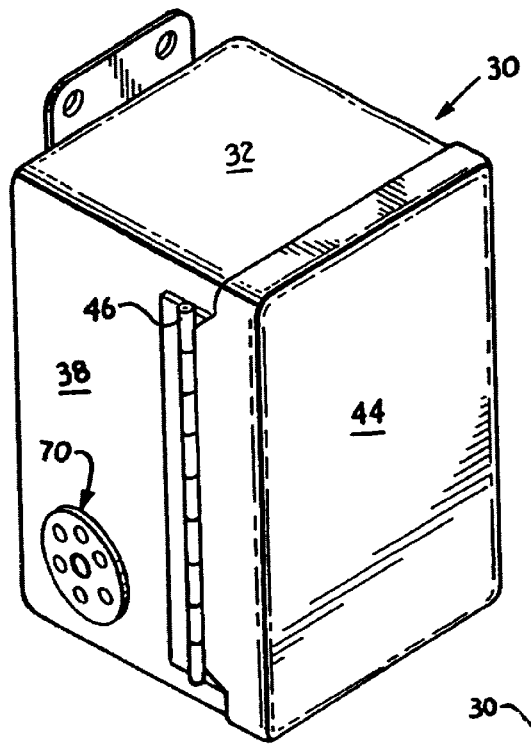
FIG. 1 is an upper, left side perspective view of the sensor housing embodying the present invention.
Figure 2:
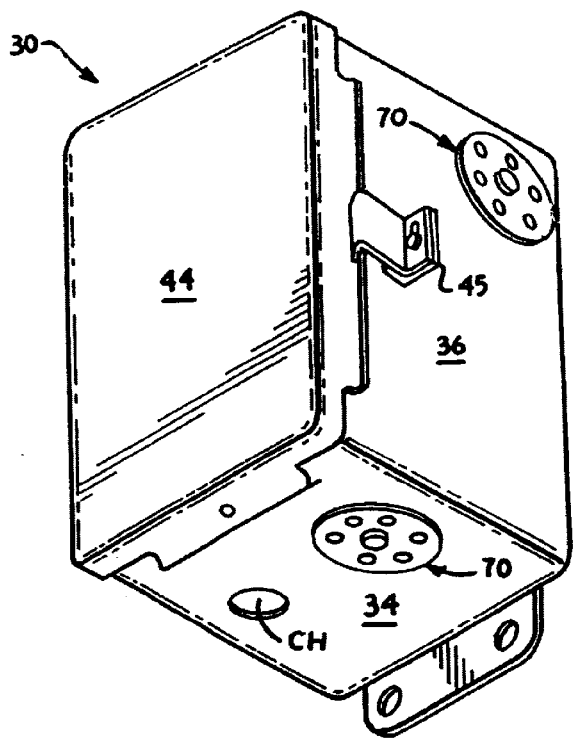
FIG. 2 is a lower, right side perspective view of the sensor housing.
Figure 3:
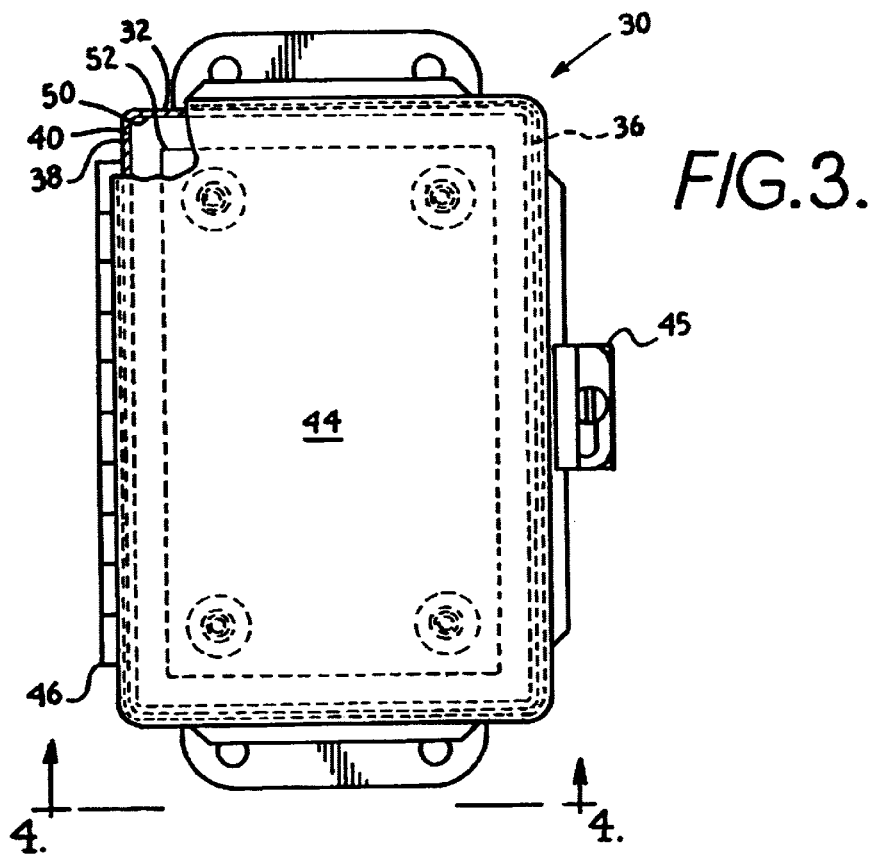
FIG. 3 is a front view of a sensor housing.
Figure 4:
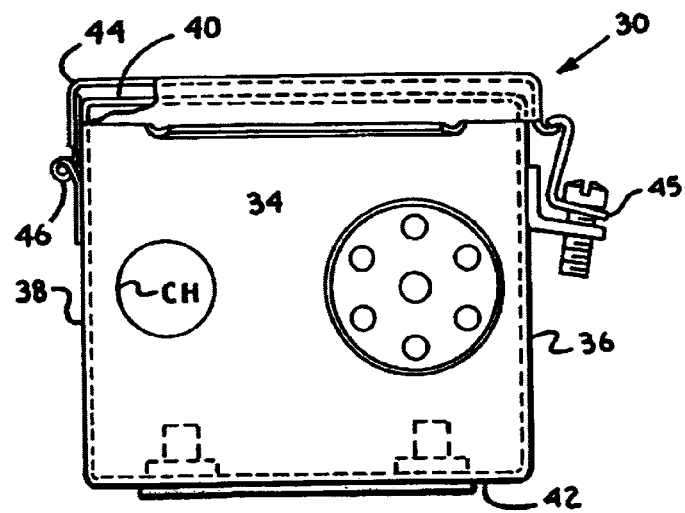
FIG. 4 is a bottom plan view of the sensor housing.
Figure 5:
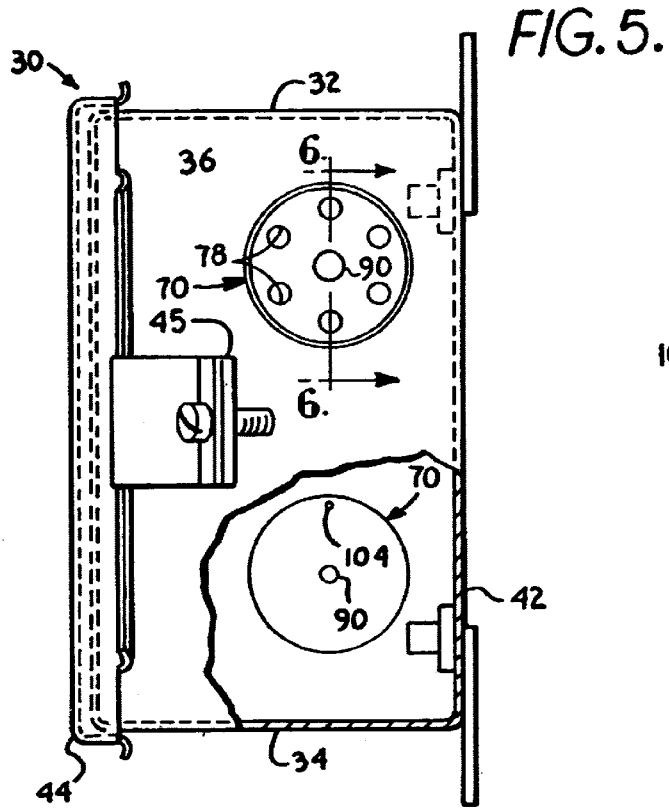
FIG. 5 is a right side elevational view of the sensor housing with a portion broken away showing the left side vent hole/vent plug combination included in the monitoring system of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The monitoring system embodying the teaching of the present invention maintains desired conditions in the vicinity of a condition monitoring sensor and components related thereto by maintaining temperature within a desired range and permitting fluid circulation past the sensor and the related components. Fluid circulation provides an efficient mechanism for removing contaminants or other undesired elements from the vicinity of the sensor and/or the components associated therewith. By permitting ambient atmosphere circulation into, through and out of the housing, precise and reliable readings can be obtained using the monitoring system of the present invention. The several elements discussed hereinbelow can be used with any monitoring system, including the aforementioned model GM-10 and model EC systems.

The monitoring system of the present invention preferably includes a housing 30 to contain circuit 10. A housing 30 used in the monitoring system of the present invention is shown in FIGS. 1–5. Referring to FIGS. 1–5, it can be seen that housing 30 includes a top 32, a bottom 34, sides 36 and 38, a front 40 and a rear 42. Front 40 is open and is covered by a door 44 that is hingeably mounted on the housing to open and cover front 40 and which is mounted in a closed condition by a lock system which includes an element 45 or the like mounted on side 36 of housing 30. A hinge 46 fixes door 44 to side 38 of housing 30. Housing 30 has an inside surface 50 (best shown in FIG. 6) on which circuit 10 is mounted, preferably on the rear 42 for easy access via open front 40. Insulation 52 can be placed on the inside surface 50 if necessary.

Housing 30 is formed of materials that are suitable for use in the selected environment, and can be formed of steel or other such material that satisfy applicable codes and standards. One preferred material is 16 gauge metal such as painted or stainless steel; however, other materials can be selected as necessary and suitable. In some instances, explosion-proof features can be included for housing 30. NEMA (National Electrical Manufacturers Association) Class 1 construction is generally satisfactory for the housing 3 due to its flow-through, heater-induced plume feature. However, housings enclosures for the sensor 12 can be constructed to other NEMA criteria where applicable.

While sensor 12 has been shown inside housing 30, it is noted that the sensor, or one or more of the sensors 12' can be positioned outside housing 30 without departing from the scope of the present disclosure. Placement of the sensor outside the housing affects the response and operation of the sensor. Furthermore, the thermostat can exercise control of the heater element at various levels. That is, when the temperature adjacent to the heated area reaches a first level, the heater is activated to a level corresponding to the first temperature level, if the temperature moves to a second level, the heater element is activated according to that second level, and so forth. This is particularly true if the temperature controlled element, such as the sensor, is located outside housing 30.

Figure 6:
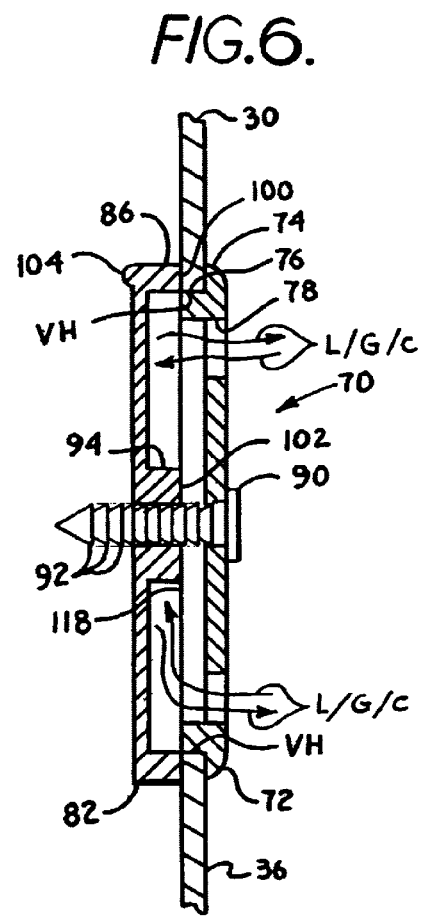
FIG. 6 is an enlarged, fragmentary, cross-sectional view of the vent hole/vent plug combination.

The monitoring system of the present invention permits fluid to circulate into, through and out of housing 30 to co-operate with the heater element or heater elements to maintain the environment in the vicinity of circuit 10 and/or sensor 12 in a desired range or ranges. To this end, in addition to a cable hole CH, housing 30 includes at least one vent hole VH defined through housing 20. Fluid can flow through vent hole VH. In order to control movement of fluid through the vent hole, a vent plug 70 is attached to housing 30 adjacent to vent hole VH. In general, the vent plug 70 includes an outer portion 72 mounted on housing 30 and an inner portion 82 attached to the outer portion 72 of the vent plug 70 and spaced from the outer portion of the vent plug 70 when the vent plug 70 is mounted on housing 30. The inner portion 82 of the vent plug is spaced from housing 30 when the vent plug is mounted on housing 30 to define a gap 118 between the inner portion 82 of the vent plug and housing 30 (FIG. 6). Ambient atmosphere flows through the gap 118. Such circulation can be used to keep the elements dry and free of condensation as discussed above. This circulation can be controlled and will be discussed in greater detail below.

Referring to FIGS. 1–5, housing 30 is shown to include vent hole/vent plug combinations 60, 62, and 66 in side 36, bottom 34, and side 38 respectively. While these particular vent hole/vent plug combinations are preferred, other locations can be used without departing from the scope of the present disclosure. More or fewer than four vent hole/vent plug combinations can also be used without departing from the scope of the present disclosure.

Figure 7:
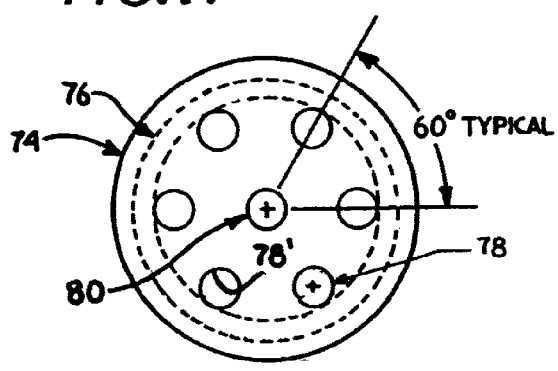
FIG. 7 shows an outer portion of a vent plug included in the monitoring system of the present invention.
Figure 8:
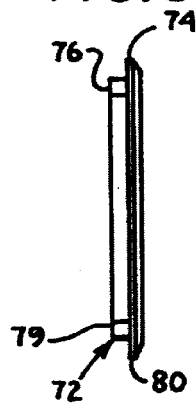
FIG. 8 is a side elevational view of the vent plug outer portion shown in FIG. 7.

Referring to FIGS. 6–10, preferred form of the vent plug 70 embodying the present invention is shown. Vent plug 70 comprises an outer portion 72 (best shown in FIGS. 7 and 8) which has an outer perimeter 74 which is circular in the preferred form of the invention, but could be other shapes if suitable, an annular neck 76 spaced radially inwardly from outer perimeter 74 of the preferred form of vent plug 70, a plurality of holes or vent openings, such as hole 78 defined through outer portion 72, and a bore 80 defined through outer portion 72 near the center thereof in the preferred form of the vent plug. As shown in FIG. 7, holes 78 are evenly distributed and evenly spaced apart on outer portion 72. In the preferred form of the vent plug, holes 78 are spaced apart by a center-to-center arc spacing of 60° so there are six holes 78 included in outer portion 72. The reason for such arcuate spacing between holes 78 will be understood from the following discussion. Annular neck 76 is sized between a rim 79 and the inner surface of outer perimeter 74 to be essentially equal in size to the thickness of housing 30 and is diametrically sized to snugly engage the housing 30 adjacent to the vent hole VH to establish a friction fit between outer portion 72 and the housing 30 that securely mounts outer portion 72 on housing 30. A lip 80 between neck 76 and outer perimeter 74 abuts the outer surface of housing 30 adjacent to vent hole VH when the vent plug is in place on the housing to further ensure proper seating of the vent plug 70 on the housing 30.

Vent plug 70 further includes an inner portion 82 (best shown in FIGS. 9 and 10) which includes an outer perimeter 84 which has essentially the same dimensions as outer perimeter 74 of the outer portion 72. As mentioned above, the preferred form of the vent plug 70 being discussed has a circular outer perimeter; however, other shapes can be used without departing from the scope of this disclosure. Vent plug inner portion 82 further includes a spacing element 86 on inner portion 82 near outer perimeter 84 and a bore 88 defined through inner portion 82 and located centrally thereof to be aligned with bore 80 defined through outer portion 72 when vent plug 70 is assembled. When the vent plug 70 is assembled with spacing element 86 on inner portion 82 abutting outer portion 72 to space inner portion 82 from outer portion 72, a gap 118 (best shown in FIG. 6) is defined between inner portion 82 and outer portion 72 whereby fluid can flow through the gap 118 and through holes 78 defined through outer portion 72.

The preferred form of the vent plug 70 further includes a boss 94 located on inner portion 82 and surrounding bore 88. A fastener 90 includes annular, beveled rings designed for one-way insertion through the bores 80, 88 and for resisting pull-out therefrom. Boss 94 is sized to abut outer portion 72 when spacing element 86 abuts outer portion 72 to securely seat the inner and outer portions against each other when the fastener is engaged with the aforediscussed threaded bores. That is, in the preferred form of the vent plug, top rim 100 of spacing element 86 and top rim 102 of boss 94 are coplanar with each other.

One form of the vent plug includes a tab 104 located on the inner portion 82 adjacent to spacer element 86. The tab 104 is located in a prescribed position relative to other elements of the vent plug and thus can be used to orient the vent plug in place on housing 30. For example, in one form of the invention, tab 104 is oriented at a twelve o'clock position (i.e. top dead center) for a vent plug 70 positioned in a side of the housing 30.

Still referring to FIGS. 9 and 10, it is seen that inner portion 82 further includes a trough 110 mounted thereon adjacent to outer perimeter 84 of inner portion 82. Trough 110 extends along the outer perimeter, and in the preferred form of the vent plug, is arcuate. Trough 110 extends for approximately 120 degrees along outer perimeter 84 and includes two ends 112 and 114 that extend inward of inner portion 82 on secants with respect to centrally-located bore 88.

As can be understood from this disclosure, since holes 78 are spaced apart by sixty arc degrees, and trough 110 extends for sixty arc degrees, at least one hole 78 will always be located adjacent to trough 110. This relative positioning of holes and trough to orient at least one hole 78 adjacent to trough 110 permits efficient drying of housing 30 by locating any fluid that may be collected in the trough close to a hole through which vapor associated with the collected fluid can flow thereby drying the inside of housing 30 via evaporation. The temperature inside housing 30 can be controlled to encourage or even speed up this evaporation by use of heating element 20.

It is noted that control of the internal housing environment as well as the direction and volume of fluid flow through the housing can be exercised by controlling the size of the gaps 118 in each vent hole/vent plug combination as well as the number, relative placement and spacing of the vent hole/vent plug combinations. Preferably, the vent plugs 70 are formed of a plastics-type material which is amenable for use in the environment of interest.

Referring to FIG. 6, operation of the vent hole VH/vent plug 70 combination of the present invention is illustrated. Fluid, such as gas G or liquid L, or a combination C thereof, flows into, through and/or out of housing 30 via the vent hole VH/vent plug 70 combinations and gaps. The arrows are designated L/G/C to indicate the various combinations of fluid states that can be accommodated by housing 30 (FIG. 6). As discussed above, permitting fluid to flow into, through and/or out of housing 30 and accounting for such fluid flow permits the monitoring system of the present invention to maintain environmental conditions inside housing 30 within desired ranges. When such fluid flow feature is combined with housing temperature control associated with heater element 20, sensor readings can be very reliable.

Referring to FIG. 11, the basic circuitry used in the monitoring system of the present invention is shown as circuit 10. Circuit 10 includes a sensor 12 suitably connected to the remainder of the circuit. The circuitry associated with sensor 12 is safe, highly specific to the monitored fluid, exhibits rapid response time, has a long life, and can be modular for ease of installation. The abovementioned model GM-10 also includes circuit elements which permit that monitoring system to monitor a plurality of zones and to be combined with other monitoring systems for further versatility, has setpoints that are easy to adjust, has system diagnostic features, is connectable to Ethernet networks, has various displays, including bargraph displays, has LEDs for system and relay status identification, has time delayed relays, has user-selectable latching or non-latching alarms, has calibration by-pass mode, has built-in fault circuitry and can conform to all and any standards required. It is noted that other than the elements specifically discussed herein, the basic circuit elements included in circuit 10 are known to those skilled in the art based on the teaching of this disclosure and thus will not be discussed in detail. However, for the purposes of the present disclosure, it is noted that readings from sensor 12 are suitably conditioned and transformed into signals that can be forwarded via electrical connectors, such as electrical connectors 14, to the remaining portions and elements of circuit 10 and from there to suitable monitoring, control and/or alarm systems which can include computers, communication systems and the like via landlines or via over-the-air communications systems as suitable. As shown in FIG. 11, suitable test circuits are also included in circuit 10 and include test buttons 16⁻ and 16⁺, as well as suitable microprocessors, resistors, and the like.

As discussed above, sensors used to monitor fluids such as gas and the like can be sensitive to temperature of the environment surrounding the sensor and/or the elements associated therewith. If the temperature is out of a specified range, sensor readings may be slow or even inaccurate, unreliable, imprecise and/or non-repeatable. At the very least the readings may be suspect. Accordingly, the monitoring system of the present invention includes a heater element 20 which is spaced from sensor 12 so as not to damage that sensor by unduly exposing it to heat or heat/cool cycles. Heater element 20 can include a heat generating resistor and is electrically connected to a source of power (not shown) and to a thermostat 22. Thermostat 22 is an off-the-shelf element and thus will not be further discussed. Thermostat 22 is located near sensor 12 to maintain temperature adjacent to sensor 12 to be within a desired range. However, thermostat 22 can be located anywhere on or near circuit 10 to provide temperature control of any or all of the elements in circuit 10, not just sensor 12, to remain within a desired temperature range. Circuit 10 can be mounted on a board that controls the transfer of heat to the interior of a housing and to the circuit. The desired temperature range keeps the sensor and its associated elements as dry as desired and keeps the atmospheric conditions in the vicinity of circuit 10 and/or sensor 12 within the desired range and also keeps the humidity in that area within a desired range. Any state condition that is related to temperature can be controlled using heater element 20.

The thermostat can be set according to the use being made of the monitoring system. Thus, thermostat 22 can be set to one range if sensor 12 will be exposed to an ammonia environment, another range if sensor 12 is used in a refrigerated environment, an indoor environment, an outdoor environment, a dusty environment, and the like. Those skilled in the art will understand what ranges are appropriate based on the teaching of the present disclosure. Heater element 20 can also be selected for the desired ranges, which can be 100 F.° or more in certain situations. Heater element 20 is also located to keep it as dry and clean as possible while still carrying out its intended function in order to keep it efficiently functioning as will be understood by those skilled in the art. It is also noted that the overall design of the monitoring system of the present invention contributes to this requirement as well as will be understood from the present disclosure.

While only one sensor is shown in FIG. 11, it is understood that the monitoring system of the present invention can include a plurality of sensors as indicated by sensors such as sensors 12' in FIG. 11. Each sensor can be element specific to provide an overall versatility to the overall monitoring system. Furthermore, additional heater elements, such as heater elements 20' can be included as well as additional thermostats, such as thermostats 22', to increase accuracy and/or versatility of the monitoring system. Heater elements, thermostats and sensors can be located in any suitable arrangement or relative positions to efficiently and accurately carry out the monitoring function of the system. Thus, for example, some elements can be spaced apart from each other, while other elements are stacked on each other and yet other elements are located immediately adjacent to each other. Some elements can be oriented parallel to adjacent elements while others are located at an angle with respect to adjacent elements. In this manner, a range of monitored elements, ranges, conditions and combinations can be accommodated by the monitoring system of the present invention. Heater elements can be paired with thermostats and pairs located near specific circuit elements, including sensors, as necessary to establish desired conditions, both overall and at specific locations.

In certain situations, the environment adjacent to circuit 10 is at a pressure and temperature corresponding to the dew point of one or more gases in the environment being monitored. In such situations, the sensor or other circuit elements may have liquid on them which may affect sensor readings. For the present purposes, concentration is a measure of the mass of a particular element present in a mixture and temperature does not affect certain gas concentrations for the purposes of this disclosure. Therefore, if the monitoring system is being used to monitor gas concentration, the temperature of a sensor can be changed without changing the gas concentration readings of the monitoring system. However, raising the temperature around the sensor circuitry may avoid undesired condensation of liquid on the sensor or other circuit elements and raising the temperature adjacent to the circuit 10 or adjacent to sensor 12 may prevent undesired condensation on those elements. In some cases, condensation on a sensor may chemically react with the sensor and create an adverse effect on the sensor readings and/or on the sensor itself, as by corrosion. Therefore, accurate readings of concentrations can be taken using the sensor by using a heater element to keep the temperature of the sensor and/or its related elements in a desired range while also protecting the sensor and its related elements from undesired conditions, such as degradation, chemical reactions or the like that may occur between a liquid and a circuit element or between liquids in a mixture of liquids and the monitoring system elements.

It is to be understood that while certain forms of the present invention have been illustrated and described herein, it is not to be limited to the specific forms or arrangement of parts described and shown.

What is claimed and desired to be secured by Letters Patent is as follows:

1. A vent plug for use on a housing for electrical components comprising:
 a) an outer portion which includes:
  (1) an outer perimeter,
  (2) an annular neck spaced from the outer perimeter;
  (3) a plurality of holes defined through said outer portion, and
  (4) an attaching element-accommodating bore defined through said outer portion;
 b) an inner portion which includes
  (1) an outer perimeter,
  (2) a spacing element on said inner portion, and
  (3) an attaching element-accommodating bore defined through said inner portion; and c) an attaching element attaching said inner portion to said outer portion when the vent plug is assembled with the spacing element on said inner portion abutting said outer portion to space said inner portion from said outer portion with a gap being defined between said inner portion and said outer portion whereby fluid can flow through said gap and through the holes defined through said outer portion when said vent plug is assembled.

2. The vent plug as in claim 1 wherein said outer portion is circular and at least some of the holes of said plurality of holes are arcuately spaced apart from each other.

3. The vent plug as in claim 2 wherein the holes of said plurality of holes are spaced apart from each other by approximately 30°.

4. The vent plug as in claim 1 further including a trough mounted on said inner portion adjacent to the outer perimeter of said inner portion.

5. The vent plug as in claim 4 wherein said trough extends for approximately 60° of the outer perimeter of said inner portion.

6. The vent plug as in claim 1 further including a boss located on said inner portion and which has an attaching element-receiving bore extending therethrough.

7. The vent plug as in claim 6 wherein the spacing element of said inner portion is located adjacent to the outer perimeter of said inner portion.

8. The vent plug as in claim 1 wherein the outer portion of said vent plug includes
 a) an outer perimeter,
 b) an annular neck spaced from the outer perimeter of said vent plug,
 c) a plurality of holes defined through said outer portion, and
 d) an attaching element-accommodating bore defined through said outer portion.

9. A vent plug for mounting across a vent plug opening in a housing for electrical components or gas sensors, said vent plug comprising:
 a) an outer portion adapted to be mounted against an outer surface of said housing and across the vent plug opening in the housing; said outer portion having a plurality of vent holes extending therethrough;
 b) an inner portion attached to said outer portion, said inner portion sized to cover said vent plug opening and spaced inwardly from an inner surface of said housing to define a gap between said inner portion and an inner surface of said housing, said gap opening into said housing and said inner portion being impermeable to gasses and liquids such that gasses and liquids passing through said vent holes can only flow into said housing through said gap.

10. The vent plug as in claim 9 wherein said inner portion and said outer portion of said vent plug are circular and wherein at least some of said vent holes are arcuately and evenly spaced apart from each other around a central axis of said outer portion.

11. The vent plug as in claim 10 wherein said inner portion of said vent plug includes a trough extending radially and partially around said outer perimeter of said inner portion along an arc at least as great as the angle between adjacent vent holes.

12. The vent plug as in claim 11 wherein said trough extends along an arc approximately twice as great as the angle between adjacent vent holes.

13. The vent plug as in claim 9 wherein said inner portion and said outer portion of said vent plug are circular and wherein said vent holes comprise six vent holes radially spaced apart approximately 60 degrees around a central axis of said outer portion; and wherein said inner portion of said vent plug includes a trough extending radially and partially around an outer perimeter of said inner portion along an arc of approximately 120 degrees.

14. The vent plug as in claim 9 wherein said vent plug further includes a spacing element formed on one of said inner or outer portions to space said inner portion from said outer portion to define said gap between said inner portion and said outer portion whereby gasses and liquids can flow through said vent holes and through said gap.

15. The vent plug as in claim 14 wherein said vent plug further includes an attaching element for securing said inner portion to said outer portion.

\* \* \* \* \*